United States Patent [19]

Teng et al.

[11] 4,429,174

[45] Jan. 31, 1984

[54] PROCESS FOR DEHYDROCOUPLING TOLUENE USING A MODIFIED FAUJASITE ZEOLITE CATALYST COMPOSITION

[75] Inventors: Harry H. Teng, Waldwick; I-Der Huang, Upper Saddle River, both of N.J.

[73] Assignee: Exxon Research & Engineering Co., Florham Park, N.J.

[21] Appl. No.: 405,803

[22] Filed: Aug. 6, 1982

[51] Int. Cl.³ .......................... C07C 3/62; C07C 3/00
[52] U.S. Cl. .................................. 585/426; 585/428; 585/435; 585/436; 502/79
[58] Field of Search ............... 585/426, 428, 429, 435, 585/436, 440; 252/455 Z

[56] References Cited

U.S. PATENT DOCUMENTS 4,255,604  3/1981  Williamson et al. ................ 585/428

FOREIGN PATENT DOCUMENTS 1259766  1/1972  United Kingdom ................ 585/428

*Primary Examiner*—Delbert E. Gantz
*Assistant Examiner*—A. Pal
*Attorney, Agent, or Firm*—Robert A. Maggio

[57] ABSTRACT

A process for dehydrocoupling a hydrocarbon, such as toluene, using oxygen as the oxidant, in the presence of a crystalline zeolite of the faujasite structure containing a cation such as cesium, and a promoter, such as boron and/or phosphorus is disclosed.

6 Claims, No Drawings

PROCESS FOR DEHYDROCOUPLING TOLUENE USING A MODIFIED FAUJASITE ZEOLITE CATALYST COMPOSITION

BACKGROUND OF THE INVENTION

The present invention is directed to a process for dehydrocoupling toluene using a modified zeolite composition.

Styrene is currently commercially produced from benzene in a two-step process. In the first step benzene is alkylated with ethylene to form ethylbenzene, and in the second step, the ethylbenzene is dehydrogenated to form styrene.

One of the known alternative routes for forming styrene involves the oxidative coupling of toluene to form 1,2-diphenyl ethylene (stilbene) followed by the disproportionation of the stilbene with ethylene in the presence of a catalyst to form styrene. The economic significance of the overall process scheme of the toluene-stilbene route resides in the fact that styrene can be produced from 0.5 mole of ethylene and one mole of toluene. This compares with the conventional ethylbenzene route wherein styrene is produced from one mole of ethylene and one mole of benzene. In light of the rising costs of benzene and ethylene and the environmental problems of benzene, toluene-based processes will become a more attractive route than the existing benzene-based process for styrene manufacture.

Another alternative route to styrene from toluene involves the alkylation of toluene with methanol by contact of these reactants with X- or Y-type zeolites, as described in Yashima et al in the Journal of Catalysis, Vol. 26, 303–312 (1972). However, since zeolites are capable of catalyzing a variety of reactions and therefore produce a variety of by-products, the selectivity of the toluene to styrene is very low when conducting the process in accordance with Yashima et al.

In an effort to improve the selectivity of the toluene/methanol alkylation reaction to styrene, Unland et al, U.S. Pat. No. 4,140,726 describe the use of an X- or Y-type zeolite which has been modified by a cation exchange with one or more of potassium, rubidium and cesium and impregnation with boron or phosphorus. While the modification of the zeolite improves the selectivity to styrene to some extent, the only useable by-product of the reaction is ethylbenzene, while a substantial amount of unuseable by-products are also formed. Thus, from the data reported in Unland et al, the maximum total eventual selectivity to styrene which could be achieved even if one dehydrogenates all the ethylbenzene by-product formed is only about 54% (see Table 5, Run 2 of this patent).

In contrast, the process of the present invention does not employ a side alkylation reaction of toluene with methanol. Instead, the process of the present invention relies on the dehydrocoupling of toluene to form inter alia stilbene, and diphenylethane.

In addition to its utility as an intermediate in production of styrene, stilbene, because of its unsaturated character, is very reactive and may be employed in various organic syntheses. Derivatives of stilbene are useful in the production of chemicals which may be used in the manufacture of dyes, paints, and resins. It is also useful in optical brighteners, in pharmaceuticals and as an organic intermediate.

Thus, there is substantial economic incentive to develop an economical process for producing stilbene.

The ideal reaction to stilbene from toluene is the direct dehydrocoupling reaction summarized as follows:

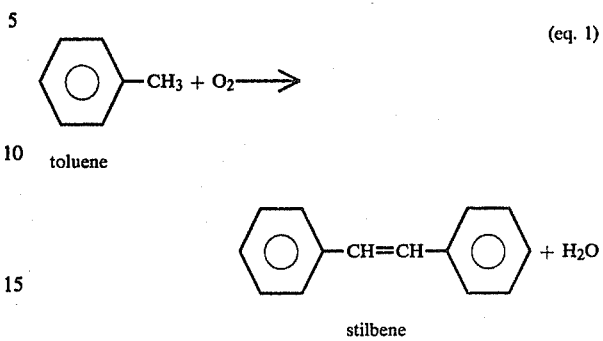

Such a selective reaction in practice is difficult to achieve. More often, the overall reaction involves the dehydrocoupling of toluene to stilbene as well as bibenzyl. Bibenzyl however can be dehydrogenated to stilbene. Furthermore when the catalysts of the present invention are employed, benzaldehyde is formed as a by-product. However, benzaldehyde can be subsequently converted to stilbene in high yield by conventional methods such as by the McMurray reductive coupling reaction using hydrogen. Thus, a commercial process for producing stilbene could include an overall reaction scheme summarized as follows:

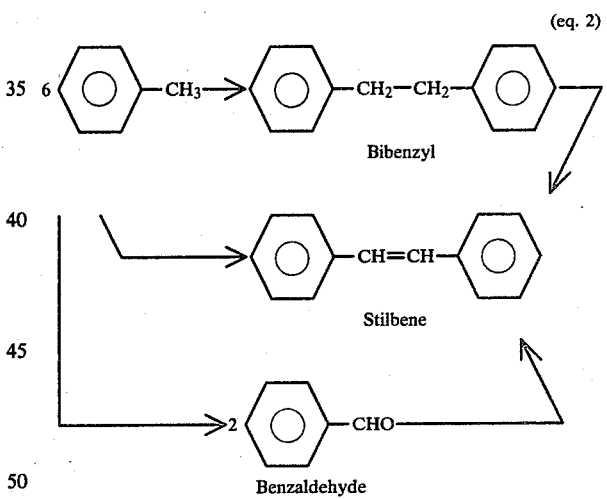

The stilbene can then be converted to styrene by the well known metathesis reaction with ethylene (see for example U.S. Pat. Nos. 3,965,206 and 4,117,021), or the stilbene can be used directly for purposes described herein above.

The reaction of Equation 1, employing oxygen as the oxidant in the absence of a catalyst, is extremely inefficient because of the preponderance of non-selective fre-radical reactions leading to complete combustion of the hydrocarbons and the formation of oxygenated by-products. Consequently, attempts have been made to improve the selectivity of the reaction using oxidants, such as metal or non-metal oxides which function in a stoichiometric mode as stoichiometric reactants providing lattice oxygen which is depleted during the reaction. Because of the oxygen depletion of metal oxide stoichiometric oxidants, their use requires that they be either very inexpensive and therefore disposable, or they must be capable of being regenerated by replacing the lattice oxygen lost during the reaction. Since many of the conventional stoichiometric metal oxide oxidants are expensive, their use requires extensive plant equipment and engineering design to provide proper regeneration. This has led to two alternative approaches; namely, fixed bed and fluidized bed systems. In the fixed bed system, two or three reactors with staggered cycles typically are employed to achieve continuous operation. This system is very costly in terms of plant equipment. In the fluidized system a single reactor can be employed and a portion of the metal-oxide can be constantly removed, regenerated, and returned to the reactor. Fluidized systems, however, lead to attrition of the metal oxide and in many instances the metal of the metal oxide can be lost as fines which foul the interior of the reactor.

To reduce the need for frequent regenerations, prior art metal oxygen compositions can also be operated in the catalytic mode.

In the catalytic mode of operation, oxygen or an oxygen-containing gas such as air or oxygen-enriched air is reacted with toluene in an amount sufficient for the dehydrocoupling reaction, the reaction being catalyzed by, and conducted in the presence of the metal oxygen composition.

Metal oxygen, compositions which operate in the catalytic mode, however, exhibit reduced selectivity and/or conversion relative to their use in the stoichiometric mode. For example, Example 6 in U.S. Pat. No. 4,091,044 illustrates the use of a Sb/Pb/Bi oxide oxidant in a stoichiometric mode. When contacted for 1 minute at 580° C. with a steam toluene feed (Run 3, Table 6) the conversion is 47.3% and a selectivity for cis and trans stilbene plus bibenzyl is 81.2%. However, after 7 minutes reaction time (Run 6, Table 6) the conversion drops to 9.7% at a corresponding selectivity of 87.5%. The substantial drop in conversion over a period of 5 minutes indicates that the oxidant is quickly deactivated. It is for this reason that the oxidant is typically regenerated for 30 to 60 minutes after each one-minute run (see Example 1, lines 34 et. seq.).

However, in Example 7 the metal oxygen composition is employed in the catalytic mode by adding air to the feed stream. While deactivation is minimal in terms of conversion after 70 minutes on-stream time, the conversion of toluene is 30%, selectivity to stilbene plus DPE is 57.6% and the selectivity to benzene plus $CO_2$ is increased from 7.1% (in Table 6, Run 6, stoichiometric mode) to 36.7% (in Table 7, Run 3). It is a disadvantage of this process that the by-products of benzene and $CO_2$ are formed in high amounts and are unuseable for subsequent conversion to stilbene.

Thus, it would be a significant improvement over conventional prior art metal oxygen compositions if a toluene dehydrocoupling catalyst could be identified which did not have to be constantly regenerated, i.e., could be used in the catalytic mode, and which also produced high amounts of stilbene or by-products which could be eventually converted to stilbene.

Representative examples of conventional metal oxide oxidants and/or catalysts are disclosed in U.S. Pat. Nos. 3,694,518; 3,739,038; 3,868,427; 3,965,206; 3,980,580; 4,091,044; 4,183,828; 4,243,825; 4,247,727; 4,254,293; 4,255,602; 4,255,603; 4,255,604; 4,268,703; 4,268,704; 4,278,824; 4,278,825; and 4,278,826 all assigned to Monsanto. These patents disclose numerous metal/oxide compositions which can be prepared by a variety of methods. None of these methods include the use of the modified zeolite catalysts of the present invention. While alumina-silica is disclosed as possible support in many of these patents, alumina-silica is amorphous in nature and is not conventionally understood to include zeolites which are crystalline in nature.

British Patent Specification No. 1,259,766 discloses a process for the oxidative coupling, of compounds which include toluene, in the presence of oxygen and a catalyst composition consisting of (1) at least one oxide of an element selected from the metals of Groups 2a (i.e., Be, Mg, Ca, Sr, Ba, Ra), 3a (i.e., B, Al, Ga, In, Tl), 4a (i.e., C, Si, Gc, Sn, Pb), 1b (i.e., Cu, Ag, Au), 2b (i.e., Zn, Cd, Hg), 3b (i.e, Sc, Y, La, Ac), 4b (i.e., Ti, Zr, Hf), 7b (i.e., Mn, Tc, Re), and 8 (i.e., Fe, Ru, Os, Co, Rh, Ir, Ni, Pd, Pt) of the Periodic Table, Bi, Cr, W, Te, Se, P, As, and Sb, and (2) at least one oxide, hydroxide, or salt of a metal of Group 1a, i.e., Li, K, Rb, Cs, and Fr (but excluding sodium oxide). The use of zeolites in accordance with the process of the present invention is not disclosed in this patent.

Commonly assigned U.S. patent application Ser. No. 387,693 filed June 11, 1982, by H. Teng, I, Huang, and H. Labowsky describes an organic method for preparing metal oxygen compositions for the dehydrocoupling of toluene. While this application discloses that such metal oxides can be applied to zeolites in general, the specific combination of exchange and promoter materials as well as the particular type of zeolites employed in accordance with the process of the present invention is not disclosed.

U.S. Pat. No. 4,192,961 discloses a process for the dehydrodimerization of toluene with oxygen to form diphenylethane and stilbene in the presence of a bismuth oxide catalyst at temperatures of 400° to 600° C., and the subsequent conversion of stilbene with ethylene to styrene in the presence of a catalyst consisting of chromium oxide, tungsten oxide, an alkali metal oxide on a silica or aluminosilicate support. The conversions of toluene are extremely low, e.g. about 4%. Furthermore, the use of zeolites for either step in the process is not disclosed in this patent.

Other literature relating to the dehydrocoupling of toluene include W. Ger. Offleg. No. 2,500,023 which discloses the use of 20% PbO on $Mg-Al_2O_3$ in a stoichiometric mode and a selectivity to stilbene and diphenylethane of 67%, and 1.8% respectively at a conversion of 41%.

U.S. Pat. No. 4,117,021 discloses the use of ZnO and PbO as catalysts for dehydrocoupling toluene.

The search has therefore continued for processes capable of dehydrocoupling toluene at relatively high toluene conversions and overall selectivity to stilbene which do not have to be frequently regenerated to maintain their activity. The present invention is a result of this search.

SUMMARY OF THE INVENTION

The present invention provides a process for dehydrocoupling a hydrocarbon selected from the group consisting of toluene, toluene derivatives, and mixtures thereof which comprises contacting said hydrocarbon with at least one oxygen containing gas, in the vapor phase at a temperature of from about 300° to about 750° C., in the presence of a catalyst composition comprising a crystalline aluminosilicate zeolite of the faujasite structure having an $SiO_2:Al_2O_3$ mole ratio of from about 2 to about 8; at least one cation selected from the group consisting of Li, K, Rb, and cesium present therein, and containing at least one promoter having a member selected from the group consisting of B, P, Pb, Cu, Zn, Ni, Co, Fe, and mixtures thereof present therein.

DESCRIPTION OF PREFERRED EMBODIMENTS

In accordance with the process of the present invention toluene or a toluene derivative is caused to undergo a dehydrocoupling reaction to form stilbene, and/or diphenylethane by contact with particular zeolite catalysts modified with selected materials.

More specifically, zeolites, which are crystalline in nature, are known for the alkylation of toluene to styrene and ethylbenzene. It has been found that in general such zeolites can be modified as taught herein to provide catalysts for the dehydrocoupling of toluene. For example, the X- or Y-type zeolites described in U.S. Pat. No. 3,251,897 and those described in the Journal of Catalysis, Yashima et al, Vol. 26, 303–312 (1972) may be employed as described herein.

In general, suitable zeolites which can be modified in accordance with the present invention will be of the faujasite structure with a $SiO_2:Al_2O_3$ mole ratio in the range of about 2 to about 8. With regard to structural classification, those zeolites with a double 6-ring or faujasite structure are generally suitable for use herein. Such zeolites characteristically have pore diameters in excess of 6 angstroms, which is appropriate for admission of toluene, and to allow exit of stilbene and diphenylethane. The X- and Y-type zeolites have been found very suitable for modification and use herein, with the X-type being particularly preferred. Type X zeolite has a typical oxide formula: $Na_2O.Al_2O_3.2.5SiO_2.6H_2O$ although the mole ratio of $SiO_2: Al_2O_3$ can typically vary from about 2:1 to about 3:1. Type Y zeolite has a typical oxide formula: $Na_2O.Al_2O_3.4.8SiO_2.8.9H_2O$ although the mole ratio of $SiO_2:Al_2O_3$ can typically vary from about 3:1 to about 6:1. Type L zeolites and natural faujasite materials are examples of other zeolites having appropriate pore size and structure for use herein. In general, zeolites having suitable properties can be utilized, whether obtainable as natural materials or prepared synthetically, and can be obtained from commercial sources or prepared by appropriate laboratory crystallization procedures.

The zeolites utilized herein are modified to have at least one cation selected from cations of Li, K, Rb, and Cs present in the catalyst. The preferred cation is cesium.

Usual ion exchange procedures can be employed to replace the sodium, hydrogen, or other ions normally present in the zeolite with the aforedescribed cations, e.g., using an aqueous Cs, Li, K or Rb hydroxide solution. However, zeolites prepared directly with the appropriate cations present therein may also be employed. In theory, 81% of sodium on type X and 71% of the sodium of type Y zeolites is exchangeable. Effective amounts of the appropriate cation can be incorporated by exchanging typically from about 0.5 to about 65, preferably from about 5 to about 60, and most preferably from about 30 to about 50% by weight of the sodium for the modifying cation. Exchanges of sodium above about 65% normally are difficult to achieve from a practical standpoint.

In addition to the aforedescribed cation modification of the zeolite, a further modification thereof is provided wherein a promoter comprising an element or compound of at least one member selected from B, P, Pb, Cu, Zn, Ni, Co, and Fe is incorporated into the zeolite. The preferred promoter is boron, phsophorus, or mixtures thereof.

The promoter serves to improve the activity and/or selectivity of the catalyst to stilbene and is employed in amounts effective to achieve such improvements relative to their absence.

Thus, while any effective amount of promoter may be incorporated into the zeolite it is contemplated that such effective amounts constitute typically from about 0.001 to about 20, preferably from about 0.01 to about 10, and most preferably from about 0.1 to about 5%, by weight of the promoter on an elemental basis, based on the total weight of the zeolite catalyst containing the promoter.

The particular form of the promoter component after incorporation has not definitely been ascertained, although it is believed to exist in the catalyst in some form of oxide which is bonded to the zeolite. Thus, preparation methods are used which result in retention of the promoter in the zeolite, and various compounds and procedures have been found suitable for this purpose. The promoter can be added to the zeolite during cation exchange procedures, or in subsequent treatments. After the promoter has been incorporated, there can be some loss by leaching or exchange, so it is generally preferred to avoid excessive washing or similar procedures subsequent to incorporation of the promoter. Also it will be undesirable to subject the catalyst to treatments known to cause loss of cations by exchange with hydrogen or other ions. Moreover, the selection of solvents for cation exchange or promoter impregnation procedures has an influence on retention of these components in the catalyst.

Solutions or slurries of the promoter in such solvents as acetone, methanol, ethylene glycol, isopropanol, isobutanol, water and mixtures thereof can be used. Alternatively, the promoter can be incorporated into the zeolite by physical admixture of the oxides therewith or with other liquid or solid compounds generally in powdered or other particulate form.

Representative sources of the promoter for use in impregnation include potassium tetraborate ($K_2B_4O_7$ in hydrated or anhydrous form), sodium tetraborate ($Na_2B_4O_7$ in hydrated or anhydrous form), boric oxide ($B_2O_3$), boric acid ($H_3BO_3$), borate esters, such as tri-methyl borate, tri-nbutyl borate, tricyclohexylborate, boron phosphate ($BPO_4$), boron phosphide (BP), borate ethers, such as trimethoxyborine $(CH_3O)_3B$, phosphoric acid and its esters, such as trimethyl phosphate $((CH_3O)_3PO)$, potassium phosphate ($K_3PO_4$), copper sulfate, copper nitrate, copper phosphate, lead nitrate, lead acetate, zinc nitrate, zinc acetate, zinc borate, nickel nitrate, nickel sulfate, nickel acetate, cobalt acetate, cobalt nitrate, iron nitrate, iron sulfate, iron acetate, and mixtures thereof.

Other forms of the promoter compounds can readily be selected which can conveniently be employed to result in incorporation thereof into the catalyst. In general any method of contacting the catalyst with the promoter in a form resulting in retention of the same in the catalyst is suitable.

While the catalyst will generally be prepared in advance of use, it is considered feasible to introduce the promoter into the catalyst along with the process feed stream, as by adding a volatile promoter compound to the reactants and contacting the catalyst zeolite material therewith, or by introducing such promoter compound with inert diluent prior to introduction of the reactants.

Alternatively, the promoter can conveniently be incorporated into the zeolite by inclusion in an ion exchange solution, or by subsequently utilizing a solution of such component as a slurrying medium for zeolite particles or as an impregnating medium to be absorbed in the zeolite. The media for incorporating the promoter do not necessarily have to completely dissolve the promoter material, and in fact may often contain suspended solids.

The modified zeolite catalyst is generally dried following impregnation procedures typically at temperatures of from about 25 to about 150, preferably from about 70 to about 120, and most preferably from about 90 to about 110° C., although drying is optional.

The modified zeolite composition is then calcined. Calcination can be conducted in a separate step or in-situ in the reactor and involves heating the modified zeolite catalyst composition.

Calcination is a heat treatment wherein the solid state structure of the catalyst is fixed. Chemical elements composing the catalyst composition are fixed in a matrix. Calcination normally is conducted at a temperature higher than the intended dehydrocoupling reaction temperatures.

Accordingly, calcination is conducted at temperatures of typically from about 350 to about 800, preferably from about 400 to about 700, and most preferably from about 500° to about 650° C. for a period of typically from about 0.5 to about 20, preferably from about 1 to about 10, and most preferably from about 2 to about 4 hours.

The atmosphere under which calcination is conducted typically comprises any one or more of air, nitrogen, argon, helium and the like. Although not essential, it is preferred that the calcination atmosphere be passed as a moving stream over the catalyst composition.

After calcination is conducted the catalyst composition can optionally be activated. Activation is a procedure wherein the catalyst activity and/or selectivity is enhanced, it is believed, by cleaning the catalyst surface and/or adjusting the oxidation states of the modifying elements. Activation is especially preferred when calcination is conducted outside the dehydrocoupling reactor, since the catalyst can become contaminated during transfer of the catalyst to the reactor after calcination and cooling thereof. If calcination is conducted in-situ followed by the feed gas stream activation would not have much of a cleansing effect. Activation involves conditioning the catalyst composition with air or other atmosphere such as nitrogen, steam, oxygen, hydrocarbon (such as toluene), an air-hydrocarbon mixture, or an air-steam mixture, at elevated temperatures. Air is the preferred atmosphere for activation. Activation typically is conducted at or below the intended dehydrocoupling reaction temperatures. Activation is therefore typically conducted by contacting the modified zeolite catalyst composition with said gaseous atmosphere at temperatures of typically from about 275 to about 700, preferably from about 450 to about 650, and most preferably from about 500° to about 600° C.

Activation times can vary typically from about 0.5 to about 48, preferably from about 1 to about 24, and most preferably from about 2 to about 16 hours. While not essential, it is preferred that such activation atmosphere also pass over the catalyst as a dynamic fluid stream.

The modified zeolite catalyst is adaptable to use in the various physical forms in which catalysts are commonly used as particulate material in a contact bed, or a coating material on monolithic structures generally being used in a form to provide high surface area. The catalyst, can if desired, be composited with various catalyst binder or support materials which do not adversely affect the catalyst or the reactions in which the catalyst is to be employed.

The modified zeolite compositions described herein exhibit unexpected activity and selectivity vis-a-vis the dehydrocoupling of toluene to stilbene.

The modified zeolite compositions of the present invention are employed as catalysts and function in a catalytic mode for the dehydrocoupling of toluene.

In the catalytic mode of operation, oxygen or an oxygen-containing gas such as air or oxygen-enriched air is reacted with toluene in an amount sufficient for the dehydrocoupling reaction, said reaction being catalyzed by and conducted in the presence of the modified zeolite composition.

The term "dehydrocoupling" and related terms are employed herein to mean that the toluene molecules are coupled or dimerized, with carbon-carbon bond formation occurring between the methyl group carbons, and the coupled molecules have lost either one or two hydrogen atoms from the methyl group of each toluene molecule. When two hydrogen atoms per molecule of toluene are lost, the carbon-carbon bond at the coupling or dimerization site is unsaturated as by dehydrogenation, that is, stilbene is the product. On the other hand, bibenzyl, having a saturated carbon-carbon bond at the coupling site, is the product when only one hydrogen atom per molecule of toluene is lost.

In general, the production of stilbene as the dehydrocoupled toluene product is preferred over the production of bibenzyl. This stated preference is due to the unsaturated character of stilbene as opposed to the saturated character of bibenzyl. As is well known in the art, the presence of the unsaturated olefinic carbon-carbon bond causes the stilbene to exhibit high reactivity, thereby facilitating its direct use as an orgaic intermediate in numerous organic syntheses. Benzaldehyde may also form as a by-product. However, benzaldehyde can be directly converted to stilbene as described hereinabove.

The process of this invention is conveniently carried out in an apparatus of the type suitable for carrying out chemical reactions in the vapor phase. It can be conducted in a single reactor or in multiple reactors using either a fixed bed, a moving bed, or a fluidized bed system to effect contacting of the reactant or reactants and the modified zeolite composition. The reactant toluene or toluene derivatives will generally be heated and introduced into the reactor as a vapor. However, the reactant may be introduced to the reactor as a liquid and then vaporized.

The oxidative dehydrocoupling reaction is preferably carried out in the vapor phase and under the influence of heat. The temperature range under which the reaction can be carried out ranges from about 300 to about 750, preferably from about 400 to about 650, and most preferably from about 500° to about 600° C.

Pressure is not critical in the dehydrocoupling process of this invention. The reaction may be carried out at subatmospheric, atmospheric, or superatmospheric pressures as desired. It will be generally preferred, however, to conduct the reaction at or near atmospheric pressure. Generally, pressures from about 1 to about 10, preferably from about 1 to about 5, and most preferably from about 1 to about 2 atmospheres can be conveniently employed.

The reaction time for the contact of the reactant with the modified zeolite composition in the present invention may be selected from a broad operable range which may vary from about 0.1 to about 10, preferably from about 0.5 to about 5, and most preferably from about 1.0 to about 4 seconds. The reaction time may be defined as the length of time in seconds which the reactant gases measured under reaction conditions are in contact with the modified zeolite composition in the reactor. The selected reaction time may vary depending upon the reaction temperature and the desired toluene conversion level. At higher temperatures and lower toluene conversion levels, shorter contact times are required.

In addition to the toluene and/or toluene derivatives, other inert substances such as nitrogen, helium and the like may be present in the reactor. Such inert materials may be introduced to the process alone or may be combined with the other materials as feed provided sufficient oxygen is also contained in the feed.

Water has been found to play a significant role in the dehydrocoupling process. Higher toluene conversions and selectivities to desired products can be obtained by including water, preferably in the form of steam, in the toluene feed stream. However, care should be taken to avoid introducing too much steam, since steam cracking of the toluene can occur thereby yielding a product effluent having an undesirably high benzene and $CO_2$ by-product content. Thus, suitable steam to hydrocarbon mole ratios in the feed stream are selected in conjunction with a particular modified zeolite composition to effect improved selectivities to stilbene and diphenylethane, and toluene conversions relative to the absence of steam. Accordingly, while any effective steam-to-hydrocarbon mole ratio may be employed it is contemplated that such mole ratio constitute typically from about 0:1 to about 10:1, preferably to about 5:1, and most preferably 2:1 to about 4:1.

Oxygen is employed as a reactant, and the reaction is conducted in the catalytic mode of operation. In the catalytic mode of operation, oxygen is supplied to the feed stream in an amount sufficient for the dehydrocoupling reaction. The actual amount of oxygen supplied may be specified as a function of the amount of the toluene or other suitable hydrocarbon component. On this basis the amount of oxygen supplied in the reaction zone is ordinarily selected to provide a hydrocarbon-to-oxygen mole ratio from about 1:5 to about 1:0.1, preferably from about 1:1 to about 1:0.1, and most preferably from about 1:0.2 to about 1:0.4.

The added free oxygen may be supplied either as oxygen or an oxygen-containing gas such as air or oxygen-enriched air.

The dehydrocoupled toluene products, stilbene and bibenzyl, as well as benzaldehyde by-product may be recovered and purified by any appropriate method and means known to the art. As noted previously, stilbene, of course, is the preferred product. If desired, bibenzyl and benzaldehyde can subsequently be converted to stilbene also by methods well known in the art or recycled back to the toluene coupling reactor.

The following examples are given as specific illustrations of the claimed invention. It should be understood, however, that the invention is not limited to the specific details set forth in the examples. All parts and percentages in the examples as well as in the remainder of the specification are by weight unless otherwise specified. Furthermore, while the following examples may be written in the present tense it is to be understood that such examples represent work actually performed.

In the following examples, selectivity and conversion are calculated as follows:

$$\% \text{ selectivity} = \frac{\text{gms. of carbon of desired product}}{\text{gms. of carbon of feed}} \times 100$$

$$\% \text{ conversion} = \frac{\text{gms. of carbon in feed reacted}}{\text{gms. of carbon in feed}} \times 100$$

All product analysis is conducted by gas chromatography.

While the present invention is described in conjunction with the dehydrocoupling of toluene, it will be understood by those skilled in the art that methyl substituted derivatives of toluene can also be employed as the hydrocarbon feed source. Thus, the hydrocarbon feed source which can be employed in the process of the present invention comprises at least one compound represented by the structural formula

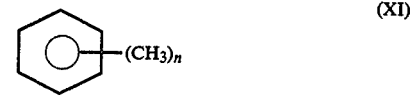

(XI)

wherein n is a number from 1 to 6, preferably 1 to 4, most preferably 1 to about 3, (e.g. 2). Representative examples of such hydrocarbon feed sources in addition to toluene, include, o-xylene, m-xylene, p-xylene, 1,3,5-trimethylbenzene, 1,2,4-trimethylbenzene, 1,2,4,6-tetramethylbenzene, hexamethylbenzene, pentamethylbenzene and the like. The most preferred toluene derivatives are the xylenes.

Generally, when a hydrocarbon feed source other than toluene is employed the dehydrocoupled product will be the appropriate methyl substituted stilbene or diphenyl ethane products, e.g. the methyl groups in excess of 1 are carried along and remain uneffected by the dehydrocoupling reactions.

The term "toluene derivative" is therefore defined herein to be at least one compound represented by formula XI wherein n is between 2 and 6.

EXAMPLE 1

This example illustrates the preparation and use of a boron promoted cesium exchanged X-type zeolite catalyst.

Two liters of an aqueous solution containing 8.5%, by solution weight, cesium hydroxide dissolved therein is prepared and divided into 3 portions of 600 cc, 600 cc, and 800 cc respectively. To the first 600 cc portion of aqueous solution is added 40 g of type-X zeolite (Lind molecular sieve 13X) to form a slurry, and the slurry is refluxed at 98°–100° C. for 18 hours. The solids of the slurry are separated from the solution and added to the second 600 cc portion of CsOH solution, and refluxed for 3 hours. The solids are again separated from the aqueous solution, and added to the remaining 800 cc portion wherein they are refluxed for 10 hours. The cesium exchanged zeolite solids are separated from the solution and dried at 120° C. in air for 18 hours.

A solution containing 25%, by solution weight, of boric acid dissolved in methanol is prepared. To 70 cc of this solution is added 10 g of the dried cesium exchanged zeolite to form a slurry which is stirred for 1 hour at 25° C. The zeolite solids were again separated from the solution by filtration and dried at 120° C. for 18 hours.

The resulting modified zeolite composition is tested by placing 4.8 g thereof in a 5 cc tubular reactor using a salt bath as a heat source. The modified zeolite is calcined for 16 hours at 600° C. while passing nitrogen through the reactor tube at a contact time of 2 to 4 sec. The calcined composition is then activated at 450° C. for 2 hours, while passing air through the reactor at a contact time of 2 to 4 sec. Upon completion of the activation, a feed stream of toluene/air/H$_2$O having a respective molar ratio of 1:3:1 is passed through the reactor at 560° C. and at a flow rate of 3600 hr$^{-1}$ GHSV. After 30 minutes on-stream time the reactor effluent is scrubbed at ice temperature and the products analyzed by gas chromatography. The toluene conversion is 20%, selectivity to stilbene is 8.8%, selectivity to diphenylethane (DPE) is 44.9% (stilbene+DPE selectivity is 53.7%), and selectivity to benzaldehyde is 37.3%. By converting the DPE and benzaldehyde to stilbene the total overall selectivity to stilbene can be as high as 91%.

EXAMPLE 2

This example illustrates the preparation and use of a cesium exchanged, boron and phosphate promoted zeolite.

A cesium exchanged type-X zeolite is prepared in accordance with Example 1. The cesium exchanged dried zeolite is then impregnated with boron phosphate by slurring 10 g cesium exchanged zeolite with 800 cc of an aqueous ammonical solution containing 5.4% ammonia, and 4.5% boron phosphate, by solution weight, dissolved therein, in accordance with the procedure of the boron impregnation step of Example 1. The ammonical solution is used to promote solubility of the boron phosphate. The solids are separated from the impregnating solution after 5 hours and dried in air at 120° C. for 18 hours.

The resulting modified zeolite composition (4.5 g) is placed into the 5 cc reactor, calcined, activated, and tested in accordance with Example 1. Product recovery and analysis is conducted in accordance with Example 1. The toluene conversion is 20%, stilbene selectivity is 19.2%, DPE selectivity is 6.1%, (selectivity to stilbene+DPE being 25.3%), benzaldehyde selectivity is 32.4%.

The principles, preferred embodiments, and modes of operation of the present invention have been described in the foregoing specification. The invention which is intended to be protected herein, however, is not to be construed as limited to the particular forms disclosed, since there are to be regarded as illustrative rather than restrictive. Variations and changes may be made by those skilled in the art without departing from the spirit of the invention.

What is claimed is:

1. A process for dehydrocoupling a hydrocarbon selected from the group consisting of toluene, toluene derivative, and mixtures thereof which comprises contacting said hydrocarbon with at least one oxygen containing gas, in the vapor phase at a temperature of from about 300° to about 750° C., in the presence of a catalyst composition comprising a crystalline aluminosilicate zeolite of the faujasite structure having an SiO$_2$:Al$_2$O$_3$ mole ratio of from about 2 to about 8, having cesium cations, and at least one promoter selected from the group consisting of B, P, and mixtures thereof present therein.

2. The process of claim 1 wherein said promoter comprises a mixture of boron and phosphorous.

3. The process of any one of claims 1 and 2 wherein the hydrocarbon is toluene.

4. The process of any one of claims 1 and 2 wherein the contacting between said hydrocarbon and the catalyst composition is effected at a temperature of from about 500° to about 600° C. for a period between about 0.5 and about 4 seconds.

5. The process of any one of claims 1 and 2 wherein steam is admixed with the hydrocarbon during said contact in an amount sufficient to provide a steam to hydrocarbon feed mole ratio of from about 1:1 to about 5:1.

6. The process of any one of claims 1 and 2 wherein the oxygen containing gas is present during said reaction in an amount sufficient to provide a hydrocarbon to oxygen mole ratio of from about 1:5 to about 1:01.

* * * * *